US007070587B2

(12) United States Patent
Meier et al.

(10) Patent No.: US 7,070,587 B2
(45) Date of Patent: *Jul. 4, 2006

(54) SECURING DEVICE FOR A LOW PROFILE GASTROSTOMY TUBE HAVING AN INFLATABLE BALLOON

(75) Inventors: Kevin C. Meier, St. Louis, MO (US); Raymond O. Bodicky, St. Louis, MO (US); Peter Von Dyck, Fernandina, FL (US); Glenn Fournie, Smithton, IL (US); Alan Ranford, St. Louis, MO (US)

(73) Assignee: Sherwood Services AG (CH)

( * ) Notice: Subject to any disclaimer, the term of this patent is extended or adjusted under 35 U.S.C. 154(b) by 48 days.

This patent is subject to a terminal disclaimer.

(21) Appl. No.: 10/170,821

(22) Filed: Jun. 13, 2002

(65) Prior Publication Data

US 2002/0177806 A1  Nov. 28, 2002

Related U.S. Application Data (63) Continuation of application No. 09/503,400, filed on Feb. 14, 2000, now abandoned, which is a continuation-in-part of application No. 09/257,164, filed on Feb. 24, 1999, now Pat. No. 6,045,536.

(51) Int. Cl.
*A61M 25/16* (2006.01)
*A61M 25/18* (2006.01)
*A61M 39/00* (2006.01)
*A61M 39/10* (2006.01)
*A61M 5/32* (2006.01)

(52) U.S. Cl. ............ 604/533; 604/174; 604/910; 128/DIG. 912

(58) Field of Classification Search ........ 604/174, 604/178, 179, 246, 247, 256, 264, 533–535, 604/537–539, 167.01–167.04; 128/912; 292/256, 256.5, 256.75, 257, 258; 403/293, 403/315, 316, 317; 24/455, 464, 466, 467, 24/477, 498, 545–547; 439/527, 529, 533, 439/540.1, 574, 575

See application file for complete search history.

(56) References Cited

U.S. PATENT DOCUMENTS

| | | | |
|---|---|---|---|
| 3,261,357 A * | 7/1966 | Roberts et al. ............ 604/105 |
| 4,233,974 A | 11/1980 | Desecki et al. |
| 4,641,646 A * | 2/1987 | Schultz et al. ......... 128/207.14 |
| 4,850,953 A * | 7/1989 | Haber et al. ................. 600/32 |
| 4,997,421 A * | 3/1991 | Palsrok et al. ............. 604/174 |
| 5,035,399 A * | 7/1991 | Rantanen-Lee ............ 251/10 |
| 5,073,166 A | 12/1991 | Parks et al. |
| 5,342,321 A * | 8/1994 | Potter ....................... 604/174 |
| 5,423,775 A * | 6/1995 | Cannon ..................... 604/533 |
| 5,549,657 A | 8/1996 | Stern et al. |
| 5,830,195 A * | 11/1998 | Peters et al. ............... 604/533 |
| 5,957,894 A * | 9/1999 | Kerwin et al. ............. 604/178 |
| 5,989,225 A * | 11/1999 | Bodicky et al. ........... 604/174 |
| 6,045,536 A * | 4/2000 | Meier et al. ............... 604/174 |

* cited by examiner

Primary Examiner—Catherine S. Williams (57) ABSTRACT

A low profile gastrointestinal tube feeding system having a securing member for securing a feeding set to a low profile gastrostomy tube disposed inside a visceral organ of a patient's body so that inadvertent removal of the feeding set from the gastrostomy tube is prevented. Also provided is a securing member that secures a connection member to an external retention member. Once the securing member has connected the connection member to the external retention member, neither the connection member nor the external retention member can be separated from one another until the securing member is first disengaged from either member.

9 Claims, 8 Drawing Sheets

SECURING DEVICE FOR A LOW PROFILE GASTROSTOMY TUBE HAVING AN INFLATABLE BALLOON

CROSS-REFERENCE TO RELATED APPLICATIONS

This application is a continuation of Ser. No. 09/503,400 filed Feb. 14, 2000 now abandoned, which is a continuation-in-part of Ser. No. 09/257,164 filed Feb. 24, 1999, now U.S. Pat. No. 6,045,536.

BACKGROUND OF THE INVENTION

1. Field of the Invention

The present invention relates to a device for use with gastrointestinal-type tubes, and more particularly to a securing arrangement for use with low profile gastrointestinal feeding systems. More specifically, the present invention relates to a securing device for securing a feeding set to a low profile gastrostomy tube.

2. Prior Art

Low profile gastrointestinal feeding systems are frequently used for long term tube fed patients who are ambulatory and/or in a combative state and require some type of gastrostomy device to provide nutrition to the stomach when a patient is unable to take nutrition orally. These gastrointestinal systems comprise a feeding set attached to a source of nutrition at one end and a low profile gastrostomy tube connected at the other end. The low profile gastrostomy tube is normally inserted through an established, matured stoma formed through the patient's abdominal and stomach walls utilizing an internal retention member deployed inside a patient's stomach or other visceral organ to anchor the free end of the gastrostomy tube thereon. The internal retention member can be either an inflatable balloon or, other retention means, such as a plurality of flexible retaining arms for affixing a hollow organ of choice, i.e. the stomach, against the posterior abdominal wall of a patient. The hollow organ is so affixed by capturing the organ wall and abdominal wall between the internal retention member secured inside the organ and an external retention member seated on the outer abdominal wall of a patient with a hollow tubular member attached between the respective retention members. The tubular member provides a fluid pathway between the feeding set connected to a source of nutrition and the internal retention member disposed inside the patient. Unfortunately, fluid flow communication between the source of nutrition and the patient may be interrupted by inadvertent removal of the feeding tube from the external retention member by a patient in a combative state or a person passing too close to the feeding set, thereby creating a critical situation where the patient may starve from lack of nutrition.

Therefore, there appears a need in the art for a securing device that securely engages the feeding set to the external retention member of a low profile gastrostomy tube so that inadvertent removal of the feeding set is prevented.

OBJECTS AND SUMMARY OF THE INVENTION

Accordingly, the primary object of the present invention is to provide a securing device for securely engaging a feeding set to a low profile gastrostomy tube.

Another object of the present invention is to provide a securing device that secures a feeding set to a low profile gastrostomy tube such that the feeding set cannot be inadvertently removed from the gastrostomy tube without first physically removing the securing device from either the feeding set or the low profile gastrostomy tube.

A further object of the present invention is to provide a securing device adapted to simultaneously engage and secure both the feeding set and the low profile gastrostomy tube.

Another further object of the present invention is to provide a securing device for use with a low profile gastrostomy tube having an inflatable balloon or a plurality of retaining arms for anchoring the gastrostomy tube inside a visceral organ.

In brief summary, the present invention overcomes and substantially alleviates the deficiencies in the prior art by providing a device designed to pass through an opening formed the wall of the abdomen and stomach or other visceral organ of a patient. The device comprises a feeding set for transporting fluid to a patient and a gastrostomy tube for providing such fluid directly to the patient's visceral organ. The feeding set includes an elongated tube having one end attached to a source of fluid and the other end attached to a connection member engaged and in fluid flow communication with the gastrostomy tube. The gastrostomy tube includes an external retention member for seating the gastrostomy tube on the outer abdominal wall of a patient and an internal retention member disposed inside a patient's stomach or other visceral organ for anchoring the gastrostomy tube therein. The external retention member is in fluid flow communication with the internal retention member through a primary lumen that forms part of a fluid pathway between a source of fluid and the gastrostomy tube. The device further comprises a securing member having opposing portions and being slidably engaged along the elongated tube with one of the opposing portions being engageable with the connection member and the other of the opposing portions being engageable with the external retention member, whereby the connection member cannot be disengaged from the gastrostomy tube without first detaching one of the opposing portions of the securing member from either the connection member or the gastrostomy tub. The securing member of the present invention is disclosed in applicant's co-pending patent application Ser. No. 09/257,164 entitled "Securing Device for a Low Profile Gastrostomy Tube" which is herein incorporated by reference.

These and other objects of the present invention are realized in the preferred embodiment of the present invention, described by way of example and not by way of limitation, which provides for a securing member for a low profile gastrointestinal feeding system that prevents inadvertent removal of the feeding set from the low profile gastrostomy tube.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
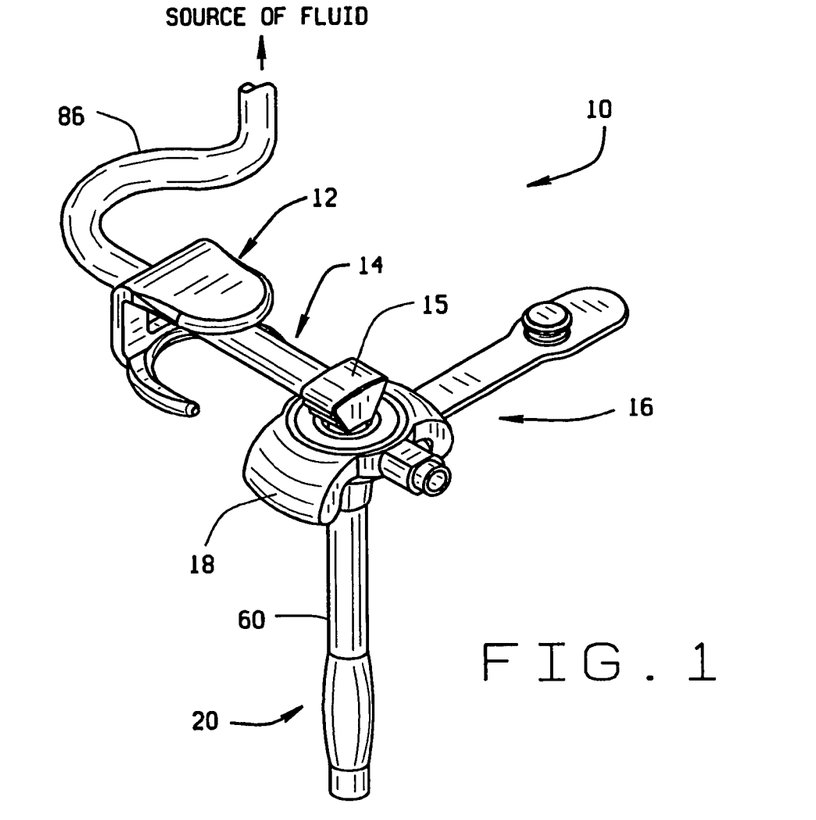
FIG. 1 is a perspective view of the low profile gastrointestinal feeding system showing the securing device slidably engaged along the elongated tube according to the present invention.
Figure 2:
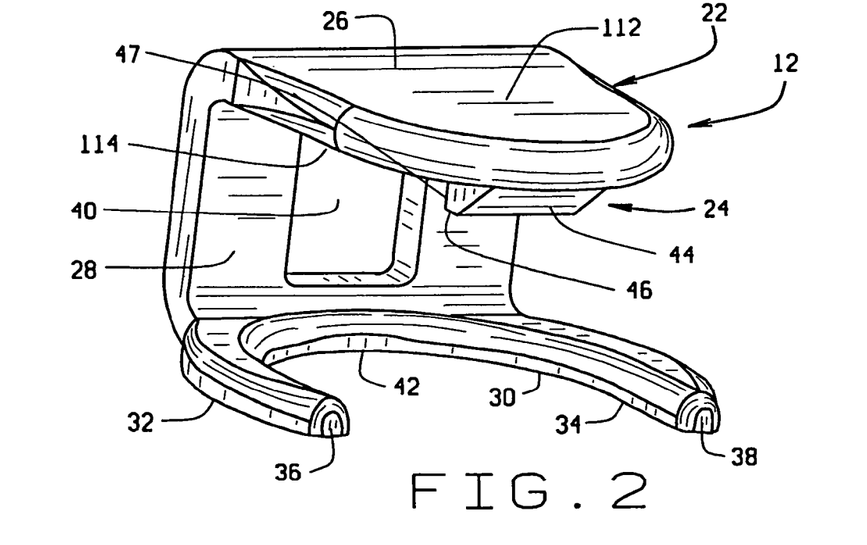
FIG. 2 is a perspective view of the securing member according to the present invention.
Figure 3:
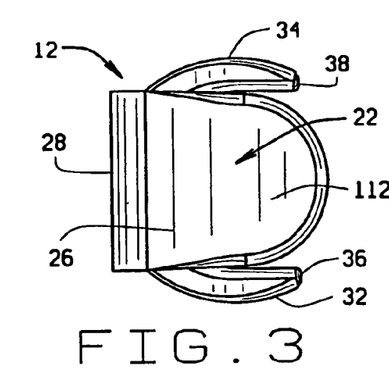
FIG. 3 is a top view of the securing member according to the present invention.
Figure 4:
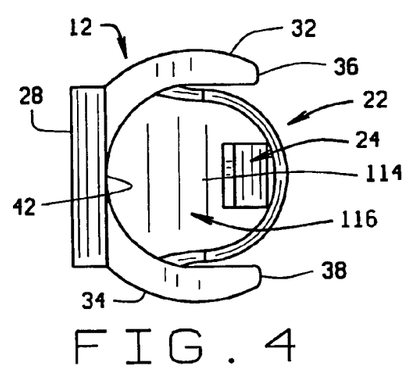
FIG. 4 is a bottom view of the securing member according to the present invention.

Referring to the drawings, the preferred embodiment of the low profile gastrointestinal feeding system according to the present invention is illustrated and generally indicated as 10 in FIG. 1. The low profile gastrointestinal tube feeding system 10 comprises a feeding set 14 attached to a low profile gastrostomy tube 16. The gastrostomy tube 16 includes an external retention member 18 for seating the gastrostomy tube 16 on the outer abdominal wall of a patient (FIG. 7) and an internal retention member 20 for affixing a hollow organ, i.e. the stomach, against the posterior abdominal wall of the patient as shall be explained in greater detail below.

Figure 8:
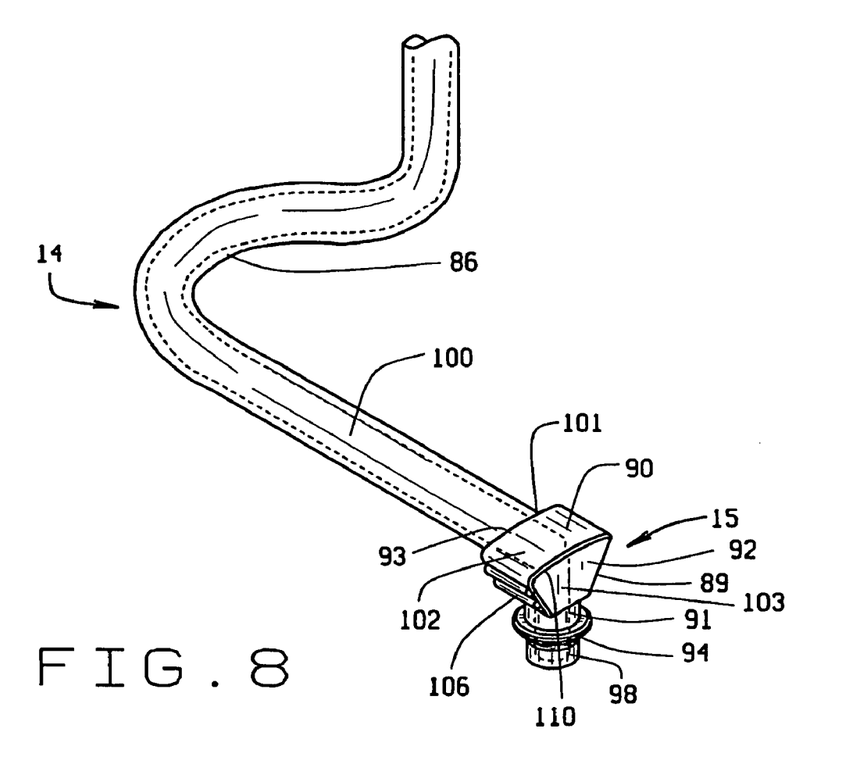
FIG. 8 is an isolated fragmentary perspective view of the elongated tube attached to a connection member according to the present invention.

Referring to FIG. 8, an isolated partial view of the feeding set 14 is shown. Feeding set 14 comprises a hollow elongated tube 86 with a lumen 100 (shown in phantom) formed through tube 86 having a first end (not shown) and a second end 101. First end of elongated tube 86 is attached to a source of fluid (not shown), for example a nutritional supplement, to be supplied directly to the patient's stomach through the low profile gastrostomy tube 16, while the second end 101 is attached to a connection member 15 which secures the elongated tube 86 to the low profile gastrostomy tube 16. The connection member 15 has a body 89 that includes opposing side grip portions 106 adapted to be gripped between a user's thumb and forefinger when attaching the connection member 15 to either the elongated tube 86 or the low profile gastronomy tube 16. The body 89 further includes opposing top and bottom portions 90, 91 and opposing front and back portions 92, 93. A horizontal lumen 102 (shown in phantom) forms a passage through one portion of body 89 and merges with a vertical lumen 103 (shown in phantom) that meets lumen 102 at approximately a 90-degree angle at an elbow 110. Lumens 102, 103 establish a fluid pathway though connection member 15 for the passage of fluid to the low profile gastrostomy tube 16 from the elongated tube 86. A tubular-shaped vertical extension member 98 extends outwardly from the bottom portion 91 of body 89 along the same downward vertical orientation as lumen 103. An annular retaining flange 94 is formed around extension member 98 and provides a means of attaching connection member 15 to external retention member 18, as shall be explained in greater detail below. Thus, connection member 15 functions as a 90-degree adapter for connecting elongated tube 86 to the external retention member 18 at a low profile relative to the patient's body.

Referring to FIGS. 1–5, a securing member 12 according to the present invention is illustrated and provides a means for securing the connection member 15 to the external retention member 18 of the low profile gastrostomy tube 16 after attachment of the connection member 15 thereto. The securing member 12 includes a body 22 that forms a top portion 26, back portion 28 and lower portion 30. The top portion 26 has flat outer and inner surfaces 112, 114 with inner surface 114 including a locking tab 24 for engaging and securing the securing member 12 to the connection member 15. Locking tab 24 includes a beveled forward part 44, a flat middle part 46 and a straight back part 47. Beveled forward part 44 forms an angled portion adapted to initially engage and ride over the rear portion 93 of connection member 15. A retention area 116 is defined along inner surface 114 between the back portion 28 and the locking tab 24 for securely engaging securing member 12 to connection member 15. The back portion 28 of securing member 12 forms an aperture 40 adapted to slidably engage the elongated tube 86 therethrough, while the lower portion 30 forms opposing arms 32, 34 having respective distal tips 36, 38 which are adapted to engage the external retention member 18. Preferably, opposing arms 32, 34 collectively have a generally curved configuration with arms 32, 34 meeting at an apex 42 located in the middle of back portion 28. However, opposing arms 32, 34 can also form a generally straight parallel configuration without departing from the spirit of the present invention.

Figures 5, 6:
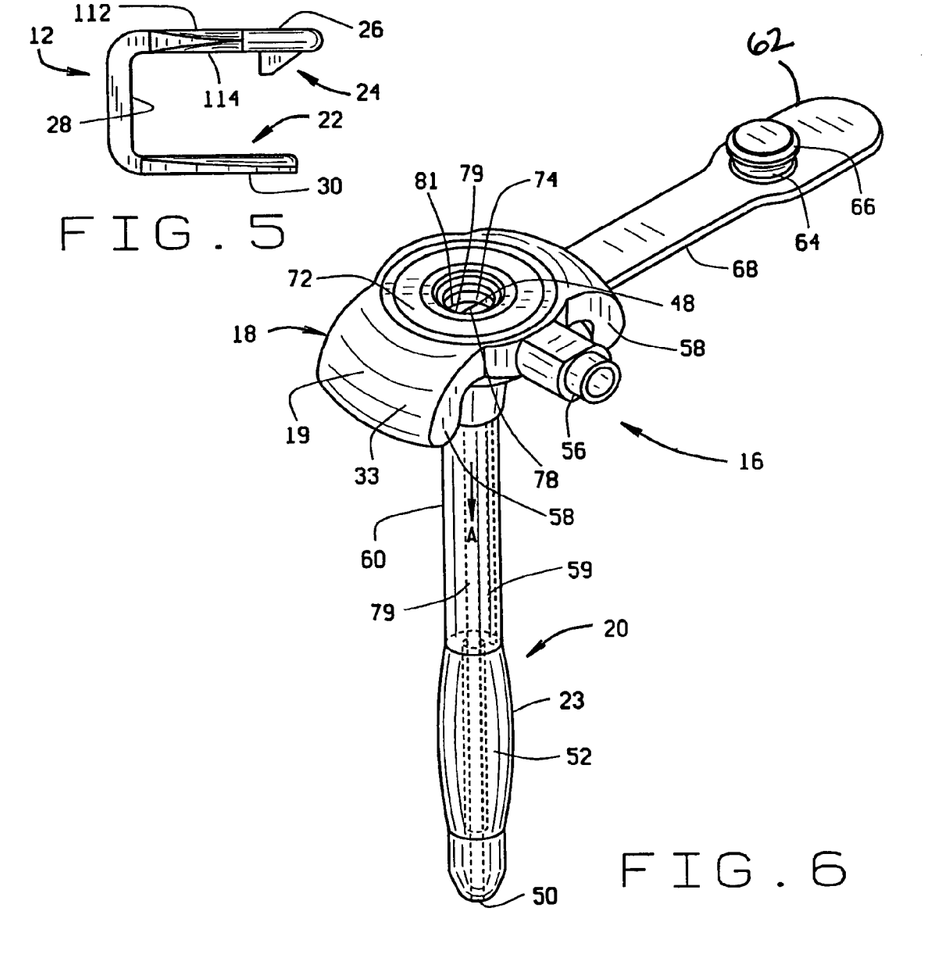
FIG. 5 is a side view of the securing member according to the present invention.
FIG. 6 is an fragmentary perspective view showing the low profile gastrostomy tube with an inflatable balloon in the deflated state according to the present invention.
Figure 7:
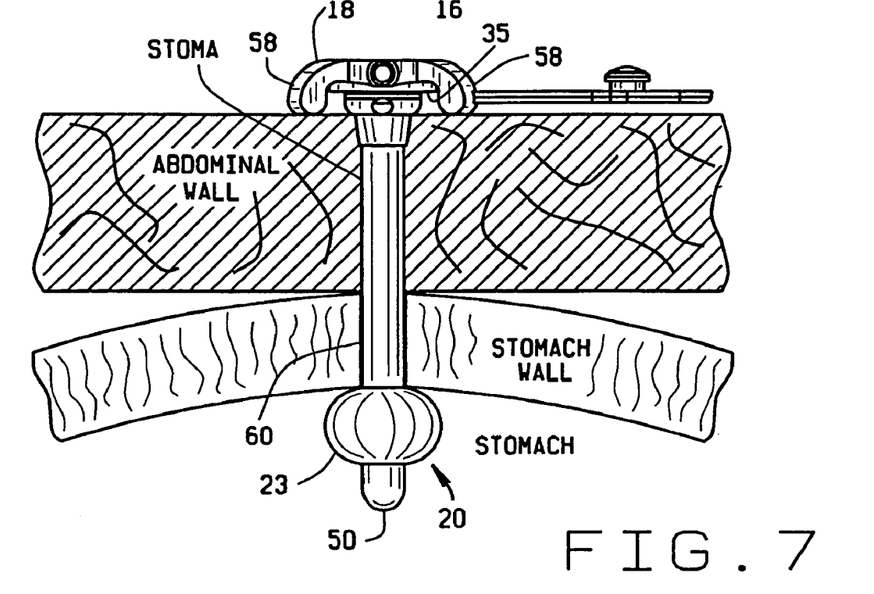
FIG. 7 is a isolated side view of the low profile gastrostomy tube passed through an opening in the visceral organ of a patient according to the present invention.

Referring to FIG. 6, an isolated perspective view of the low profile gastrostomy tube 16 is shown. The external retention member 18 includes a body 19 comprising a top surface 33 and a bottom surface 35 (FIG. 7). The bottom surface 35 forms opposing legs 58 adapted to be seated against the outer abdominal wall of a patient and to also serve to retain the external retention member 18 thereto when the low profile gastrostomy tube 16 is deployed through the stoma. The top surface 33 includes a primary lumen 79 extending through body 19 in communication with an opening 81. An annular undercut 74 is formed around the circumference of primary lumen 79 near the opening 81 for engaging either an annular flange 66 of cap member 64 for sealing off primary lumen 79 or retaining flange 94 for attaching the connection member 15 to the external retention member 18 and establishing fluid flow communication between the source of fluid and the low profile gastrostomy tube 16. The engagement of either flange 66 or retaining flange 94 with undercut 74 is preferably a snap fit engagement. However, in the alternative an interference fit or a combination of interference and snap fit engagement is felt to fall within the scope of present invention.

External retention member 18 further includes a valve member 48 spaced below undercut 74 and across primary lumen 79 for sealing off primary lumen 79 to fluid flow. Valve member 48 comprises an impermeable barrier having one or more slits 78 which provide an anti-reflux function that prevents fluid from flowing back through valve member 48 when the connection member 15 is disengaged from external retention member 18. Affixed or integrally formed with the external retention member 18 is a tethered cap 62 which includes a tether 68 that attaches cap member 64 to external retention member 18. Cap member 64 has an annular flange 66 adapted to engage undercut 74 when sealing opening 81 of primary lumen 79 to fluid flow. Annular undercut 74 is spaced above and concentrically around valve member 48. As further shown, top surface 33 of external retention member 18 also includes a retaining ring 72 which surrounds valve member 48 and provides a protective reinforcing structure around valve member 48 against manual deformation.

Figure 15:
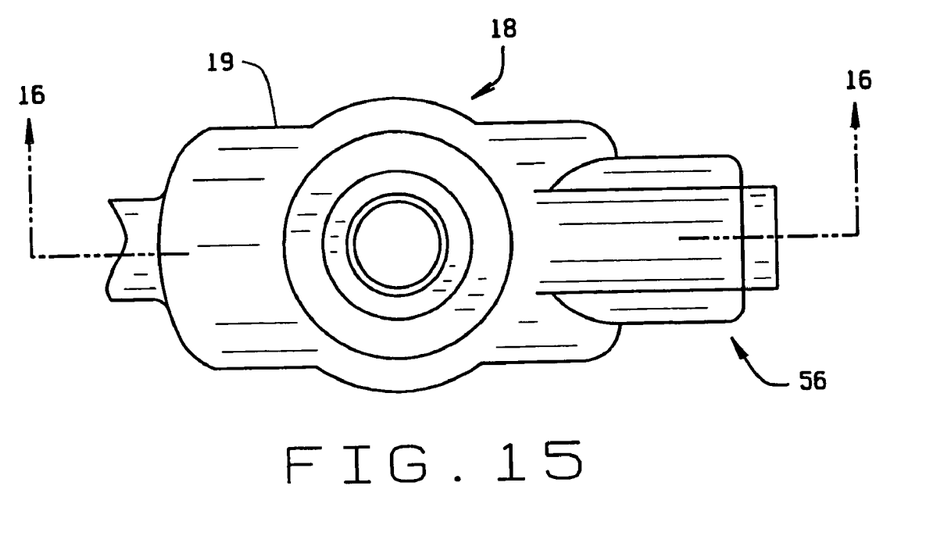
FIG. 15 is a top view of the low profile gastrostomy tube according to the present invention.
Figure 16:
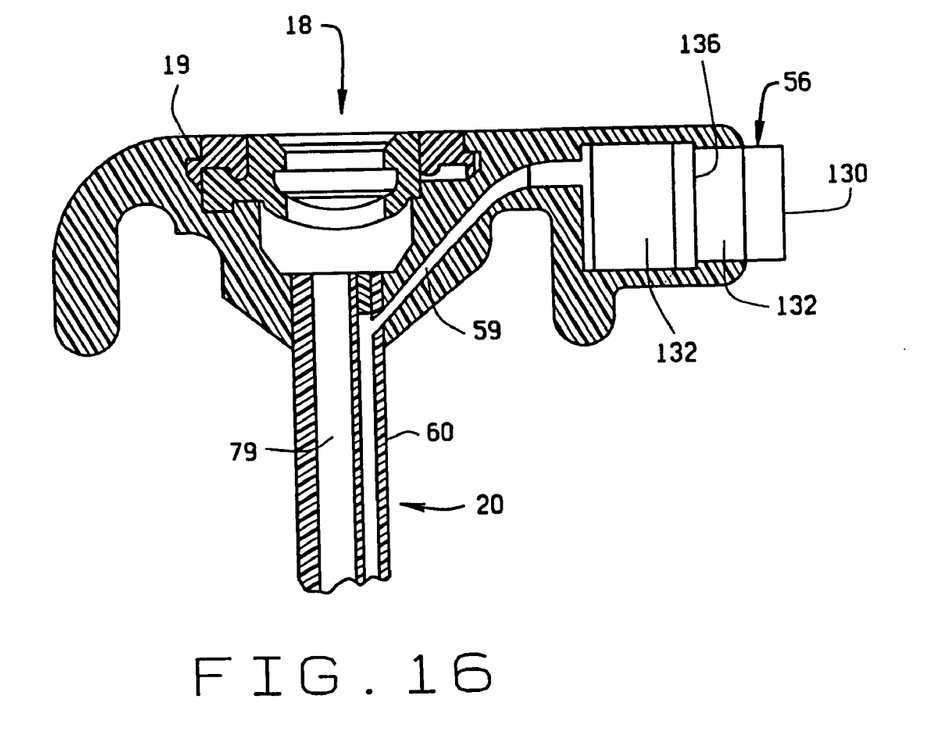
FIG. 16 is a cross-sectional view taken along line 16—16 shown in FIG. 15 according to the present invention.

Referring to FIGS. 6, 15 and 16, external retention member 18 further comprises a one way valve 56 which extends longitudinally from body 19. One way valve 56 includes an opening 130 which communicates with a passage 132 and is adapted to engage an end of a luer tip syringe (not shown) or other similar device for injecting fluid into the low profile gastrostomy tube 16 as shall be discussed in greater detail below. A valve portion 136 is interposed across passage 132 for providing a fluid tight barrier that allows fluid to enter one way valve 56 when the luer tip syringe is properly engaged thereto. However, when the end of the luer tip syringe is disengaged from the one way valve 56 valve portion 136 reseals itself, thereby preventing the escape of fluid from valve 56. Passage 132 communicates with a secondary lumen 59 that extends through external retention member 18 and into internal retention member 20 through a tubular portion 60.

Referring to FIG. 1, secondary lumen 59 extends axially through tubular portion 60 and terminates within the interior 52 of inflatable balloon 20 which is attached to or integral with tubular portion 60. Inflatable balloon 20 is constructed of an elastomeric or other flexible transparent material that permits balloon 20 to assume an inflated state when fluid is injected into the interior 52 through secondary lumen 59. As specifically illustrated in FIGS. 6 and 16, both primary lumen 79 and secondary lumen 59 (both shown in phantom) extend axially through tubular portion 60 with primary lumen 79 terminating at a distal opening 50 and secondary lumen 59 communicating with the interior 52 of inflatable balloon 20. Secondary lumen 59 provides a fluid conduit between one way valve 56 and inflatable balloon 20 for inflating and deflating balloon member 23 during insertion or withdrawal of internal retention member 20 through the stoma. To inflate balloon 20, a user engages the tip of a syringe to one way valve 56 and injects fluid into passage 132 and through secondary lumen 59. As fluid travels through secondary lumen 59 it enters the interior 52 and inflates balloon 20. To deflate balloon 20, the user withdraws the fluid from the interior 52 and through one way valve 56 by pulling pack on the plunger of the syringe until all the fluid has been fully evacuated. As further shown, primary lumen 79 acts as a conduit for the delivery of fluid directly into the patient's stomach or other visceral organ.

Figure 10:
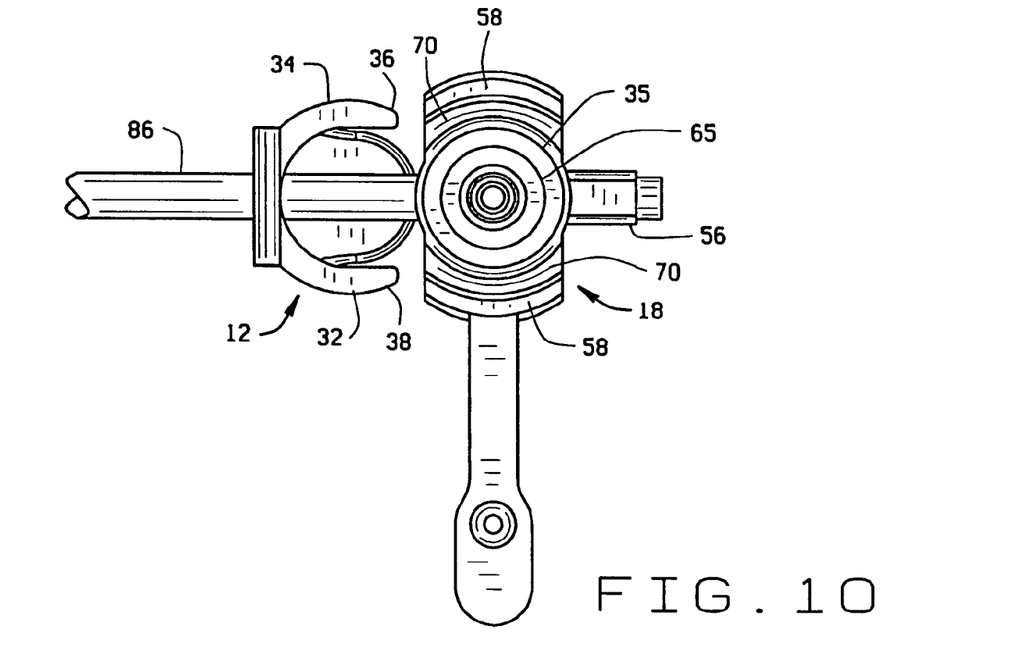
FIG. 10 is an isolated partial bottom view of the low profile gastrointestinal feeding system along line 10—10 shown in FIG. 9 according to the present invention.

A bottom view of the external retention member 18 is illustrated in FIG. 10. The bottom surface 35 of external retention member 18 includes a generally annular body 65 and two generally opposing grooves 70 which are formed between respective legs 58 and annular body 65. Opposing grooves 70 have a generally curved configuration adapted to engage and secure respective arms 32, 34 of securing member 12 when member 12 is secured to the external retention member 18 and connection member 15, as shall be discussed in greater detail below.

Figure 9:
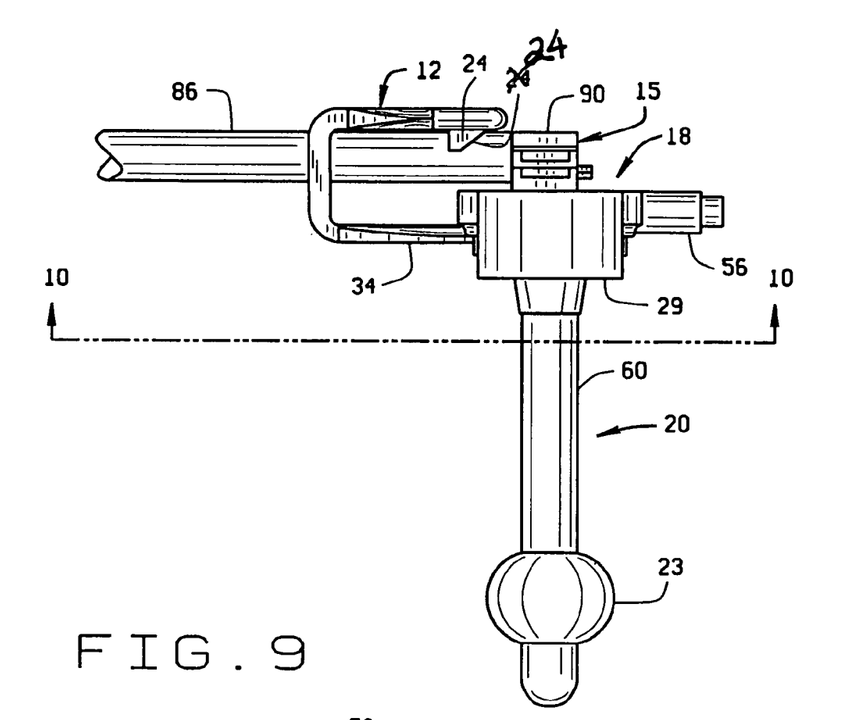
FIG. 9 is a side view of the low profile gastrointestinal feeding system showing the securing member in a pre-engagement position according to the present invention.

The method for engaging the securing member 12 to both the connection member 15 and the external retention member 18 once the low profile gastrostomy tube 16 has been properly deployed within the patient is illustrated in the sequence of positions shown in FIGS. 9–14. Referring to FIGS. 9 and 10, the pre-engagement position of the securing member 12 is shown as member 12 is slidably engaged along elongated tube 86 toward connection member 15 which is attached to external retention member 18. In the pre-engagement position, arms 32, 34 of securing member 12 are generally aligned with respective grooves 70 of external retention member 18. As the arms 32, 34 are aligned with grooves 70, the locking tab 24 of securing member 12 is also aligned with the top portion 90 of connection member 15. As the user slides the securing member 12 forwardly toward the external retention member 18, each of tips 36, 38 begin to engage respective grooves 70 of the external retention member 18, while the beveled forward part 44 of locking tab 24 concurrently approaches the top portion 90 of connection member 15.

Figure 11:
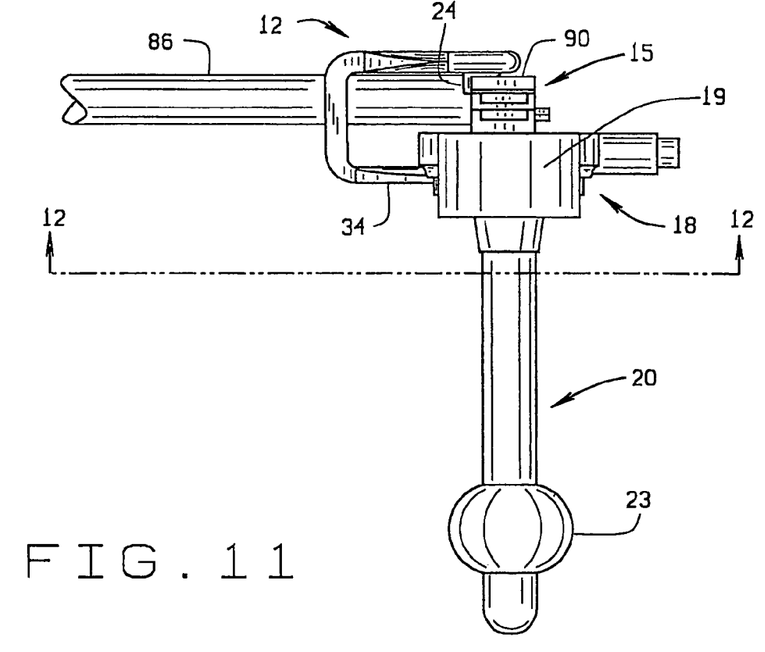
FIG. 11 is a side view of the low profile gastrointestinal feeding system showing the securing device in the engaging position according to the present invention.
Figure 12:
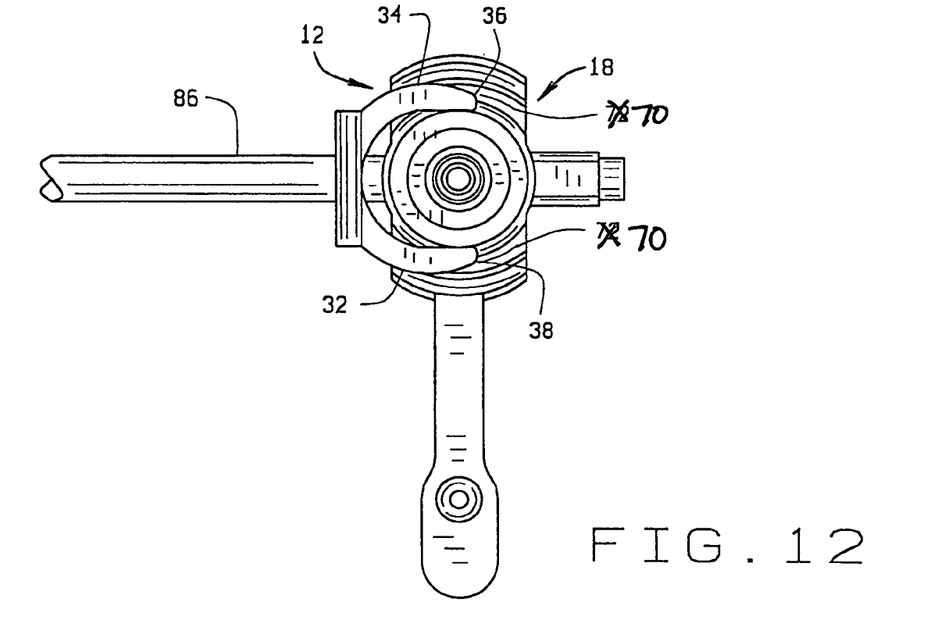
FIG. 12 is an isolated partial bottom view of the low profile gastrointestinal feeding system along line 12—12 shown in FIG. 11 according to the present invention.

In the engaging position shown in FIGS. 11 and 12, tips 36 and 38 have sufficiently entered into grooves 70 so that arms 32, 34 begin to slightly flex as arms 32,34 follow the slightly curved path formed by respective grooves 70. As arms 32, 34 engage respective grooves 70 the top portion 90 of connection member 15 rides under the beveled forward part 44 of locking tab 24 until portion 90 rides under flat middle part 46.

Figure 13:
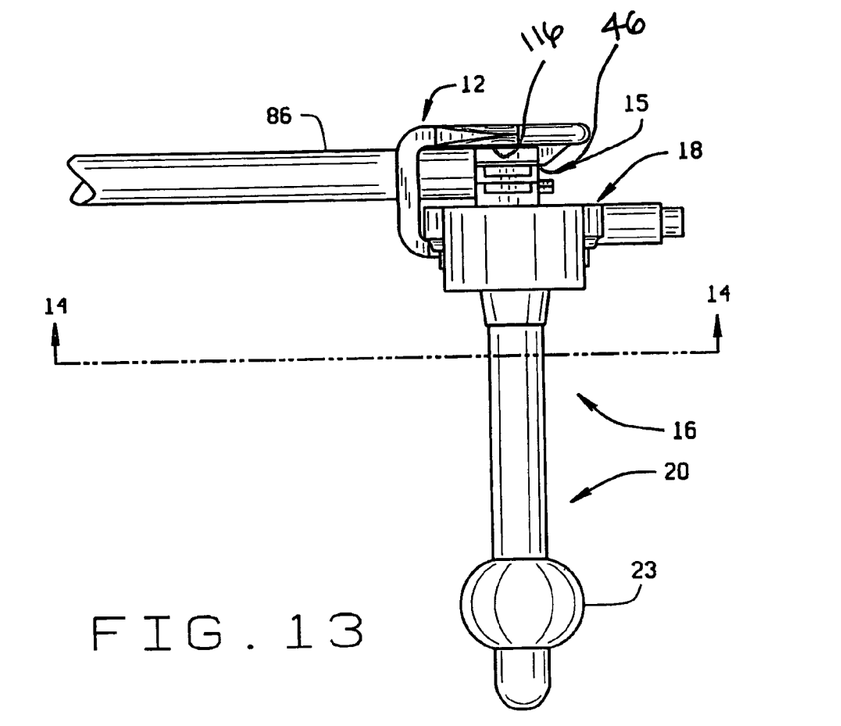
FIG. 13 is an isolated side view of the low profile gastrointestinal feeding system showing the securing device in a post-engagement position according to the present invention.
Figure 14:
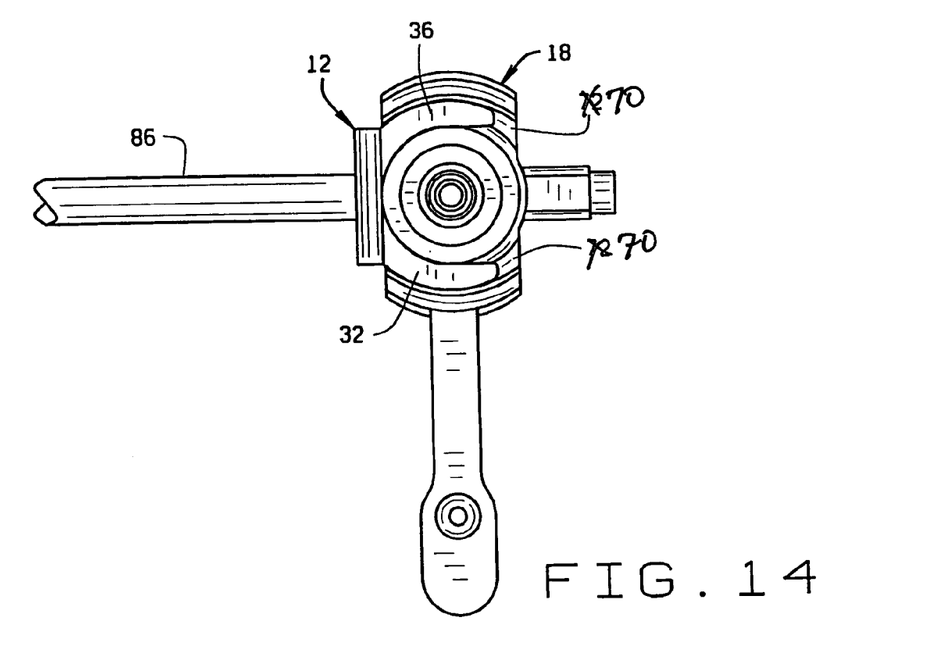
FIG. 14 is an isolated partial bottom view of the low profile gastrointestinal feeding system along line 14—14 shown in FIG. 13 according to the present invention.

In the post engagement position of securing member 12 shown in FIGS. 13 and 14, arms 32, 34 have fully engaged grooves 70. While arms 32, 34 become fully engaged in grooves 70, the top portion 90 of connection member 15 has passed under the flat middle part 46, until front portion 90 falls behind part 46 and becomes captured within retention area 116 formed between straight back part 47 of locking tab 24 and back portion 28 of securing member 12, thereby securely engaging the top portion 90 of securing member 12 to connection member 15. Neither the external retention member 18 nor the connection member 15 may be disengaged from one another without first physically disengaging the securing member 12 from either or both members 15 or 18.

Preferably, the securing member 12 is injection molded from polypropylene or other suitable medical-grade plastic that possesses sufficient flexibility and durability. However, in the alternative, stainless steel or other metal suitable for medical use is also felt to fall within the scope of the present invention.

Figure 17:
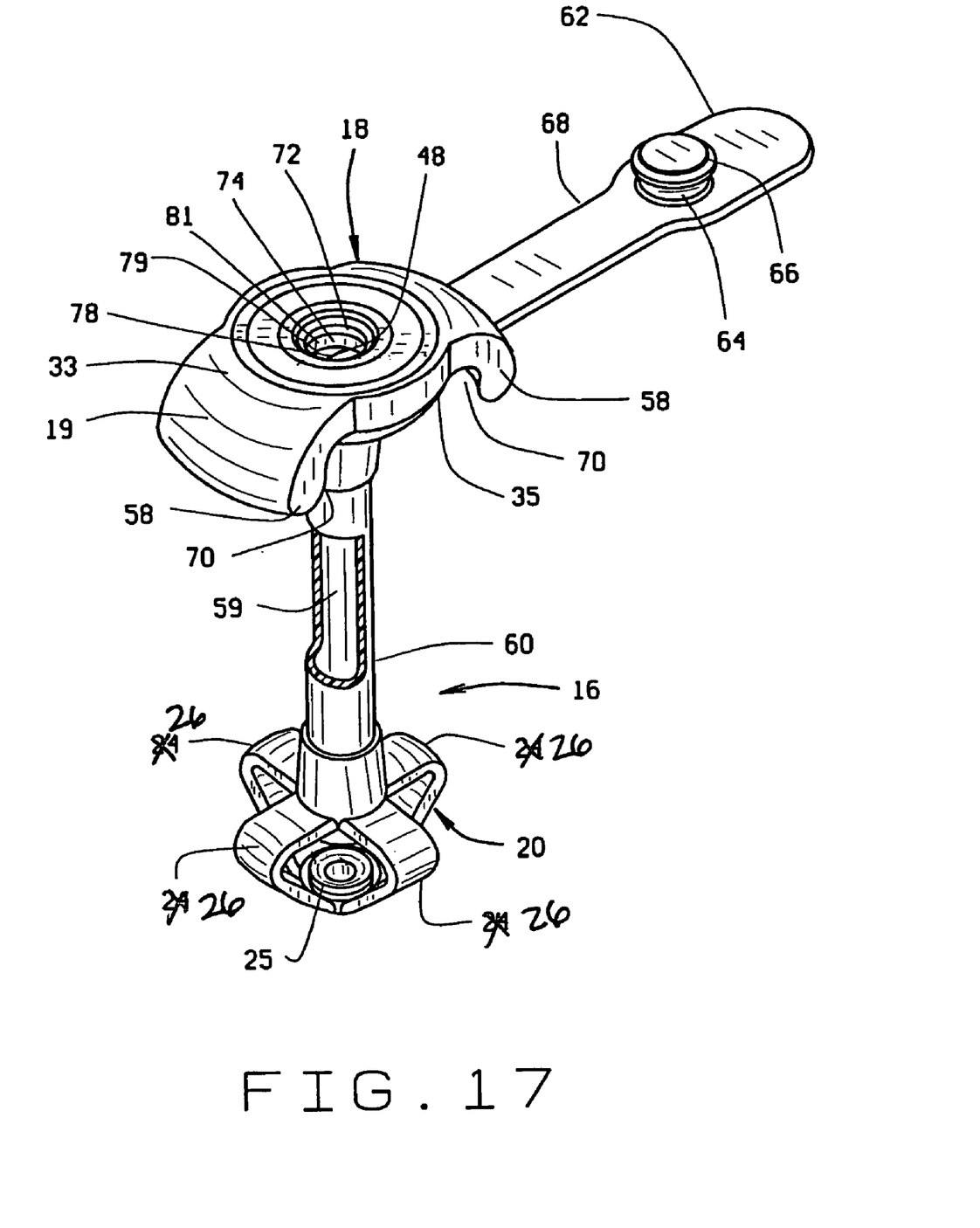
FIG. 17 is a perspective view of an alternative embodiment of the low profile gastrostomy tube comprising an internal retention member having flexible retaining arms.

Although the gastrostomy tube 16 of the present invention discloses an inflatable balloon member 23 as one means for anchoring gastrostomy tube 16 inside a visceral organ of a patient, other means of retention are contemplated by the present invention. For example, internal retention member 20 may comprise flexible retaining arms 26 in lieu of an inflatable balloon 23. As illustrated in FIG. 17, internal retention member 20 includes a tubular portion 60 extending axially from external retention member 18 with a primary lumen 59 (shown in partial fragmentary section) formed therethrough for providing fluid directly to the stomach. As further shown, flexible retaining arms 24 include an orifice 25 formed at the distal end thereof for facilitating insertion of the low profile gastrostomy tube 16 through the stoma and into the visceral organ of a patient. To insert the alternative embodiment of the low profile gastrostomy tube through the stoma, an obturator rod (not shown) is inserted through the external retention member 18 and tubular portion 60 where the rod is sufficiently registered against orifice 25 such that flexible arms 26 become extended and slenderize to a size that permits easy insertion through an established, matured stoma of a patient. Once the internal retention member 20 is inserted through the stoma and into the visceral organ, the obturator rod is withdrawn from the gastrostomy tube 16 which permits flexible retaining arms 26 to assume its preset, enlarged shape which anchors the internal retention member 20 against the wall of the visceral organ. As the internal retention member 20 is anchored, the user pulls up on the external retention member 18 such that the stomach wall contacts the posterior abdominal wall and both the abdominal and stomach walls become affixed between the retention members 18 and 20. Once the gastrostomy tube 16 is properly deployed, the connection member 15 may be engaged to the external retention member 18 and the securing member 12 secured to both the connection member 15 and external retention member 18 in the manner described above.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. A device for securing a connection member to a gastrostomy tube, said device comprising:
a unitary solid body having a back portion defining an aperture and opposing portions, one of said opposing portions being slidably engageable with the connection member, while another of said opposing portions being slidably engageable with an external retention member, said opposing portions including a top portion and a bottom portion, said top portion having a locking tab defining a beveled forward part extending towards the back portion, a flat middle part and a straight back part, said bottom portion having a pair of opposing arms said arms having free ends and adapted to engage a pair grooves on the external retention member attached to the gastrostomy tube, wherein said connection member becomes captured in an area formed between the locking tab and the back portion, and further wherein the connection member cannot be disengaged from the external retention member without first disengaging at least one of the opposing top and bottom portions from the connection member and the external retention member.

2. The device according to claim 1 said locking tab is adapted to securely engage said connection member to said device.

3. A feeding system comprising:
a feeding set, said feeding set including a hollow elongated tube having one end attached to a source of fluid and another attached to a connection member;
a gastrostomy tube including a tubular portion formed between an external retention member and an inflatable balloon, said connection member being attachable to said external retention member for establishing fluid flow communication; and
a securing member having a back portion defining an aperture, said elongated tube being slidable through said aperture and having opposing portions and being slidably engaged along said elongated tube, one of said opposing portions being slidably engageable with the connection member, while another of said opposing portions being slidably engageable with the external retention member, said opposing portions including a top portion and a bottom portion, said top portion having a locking tab defining a beveled forward part, flat middle part and straight back part, said bottom portion having a pair of opposing arms adapted to engage a pair grooves on an external retention member attached to the gastrostomy tube, wherein said connection member becomes captured in an area formed between the locking tab and the back portion, wherein said connection member cannot be disengaged from said external retention member without first detaching one of said opposing portions of said securing device from either of said connection member or said external retention member.

4. The feeding system according to claim 3, wherein said external retention member includes a body, said body forming a passage therethrough and two opposing legs, said two opposing legs forming respective grooves between each of said legs and said passage.

5. The feeding system according to claim 4, wherein said two opposing arms of said securing member are adapted to securely engage said respective grooves of said external retention member when said securing member simultaneously engages said connection member and said external retention member.

6. The feeding system according to claim 3, wherein said one of said opposing portions of said securing member includes a retention area, said retention area adapted to be slidably engaged to said connection member when the other of said opposing portions is slidably engaged to said external retention member.

7. The feeding system according to claim 3, wherein a fluid pathway is established between said source of fluid and said tubular member.

8. The feeding system according to claim 3, wherein said elongated tube attaches to said connection member at a perpendicular relationship with respect to said tubular member.

9. A method for securing a connection member attached to a gastrostomy tube, the gastrostomy tube including an external retention member seated outside a patient and a tubular member insertable through an opening formed through a visceral organ of a patient, a lumen defining a fluid pathway through the gastrostomy tube for providing fluid to the interior of the visceral organ, the connection member being attachable to the external retention member at one end and an elongated tube at the other end thereof, and a securing member having a back portion defining an aperture, said elongated tube being slidable through said aperture and being slidably engaged along the elongated tube, the securing member including opposing portions for simultaneously retaining the connection member and the external retention member together and one of said opposing portions being slidably engageable with the connection member, while another of said opposing portions being slidably engageable with the external retention member, said opposing portions including a top portion and a bottom portion, said top portion having a locking tab defining a beveled forward part, flat middle part and straight back part, said bottom portion having a pair of opposing arms adapted to engage a pair grooves on the external retention member attached to the gastrostomy tube, wherein said connection member becomes captured in an area formed between the locking tab and the back portion, the steps of the method comprising:

a) engaging the connection member to the external retention member;

b) establishing fluid flow communication between the source of fluid and the gastrostomy tube;

c) grasping the securing member and sliding the securing member along the elongated tube until one of said opposing portions engages the connection member while the other of said opposed portions engages the external retention member; and d) securing one of said opposing portions to the connection member while securing the other of said opposing portions to the external retention member such that the connection member cannot be disengaged from the external retention member without first disengaging at least one of said opposing portions.

* * * * *